United States Patent
Opitz et al.

(12) 
(10) Patent No.: US 6,224,909 B1
(45) Date of Patent: May 1, 2001

(54) FAST DECOMPOSING PELLETS

(75) Inventors: Michaela Opitz, Bad Dürkheim; Hendrik Von Büren, Nussloch; Rolf-Dieter Gabel, Schwetzingen; Geoffrey Lee, Buckenhof, all of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/147,817

(22) PCT Filed: Sep. 9, 1997

(86) PCT No.: PCT/EP97/04897

§ 371 Date: May 11, 1999

§ 102(e) Date: May 11, 1999

(87) PCT Pub. No.: WO98/10754

PCT Pub. Date: Mar. 19, 1998

(30) Foreign Application Priority Data

Sep. 12, 1996 (DE) ................................................ 196 37 082

(51) Int. Cl.[7] ................................ A61K 9/14; A61K 9/50
(52) U.S. Cl. .......................... 424/489; 424/499; 424/501; 424/494; 424/495; 424/497
(58) Field of Search ..................................... 424/490, 489, 424/484

(56) References Cited

U.S. PATENT DOCUMENTS

| | | | |
|---|---|---|---|
| 5,096,717 | * 3/1992 | Wirth et al. | 424/490 |
| 5,258,185 | * 11/1993 | Bauer et al. | 424/484 |
| 5,464,632 | 11/1995 | Cousins et al. | |
| 5,759,580 | * 6/1998 | Jans et al. | 424/489 |
| 5,817,338 | * 10/1998 | Bergstrand et al. | 424/468 |
| 5,922,341 | * 7/1999 | Smith et al. | 424/430 |
| 5,958,458 | * 9/1999 | Norling et al. | 424/490 |

FOREIGN PATENT DOCUMENTS

| | | |
|---|---|---|
| 3532692 | 3/1987 | (DE) . |
| 0421921 | 4/1991 | (EP) . |
| 92/00064 | 1/1992 | (WO) . |
| 95/28147 | 10/1995 | (WO) . |

OTHER PUBLICATIONS

"Clinical Pharmacokinetics: Concepts and Applications", M. Rowland and T.N. Tozer, p. 28 (1980).

* cited by examiner

Primary Examiner—Thurman K. Page
Assistant Examiner—Isis Ghali
(74) Attorney, Agent, or Firm—Arent Fox Kintner Plotkin & Kahn, PLLC

(57) ABSTRACT

The invention concerns pharmaceutical forms of administration that are in the form of pellets which contain a retarding agent in which the release rate of the active substance is not delayed or is substantially identical compared to corresponding pellets that contain no retarding agent. The release rate of these rapidly disintegrating pellets is at least about 90% within a time period of 30 minutes. In addition the present invention also concerns processes for the production these pellets.

26 Claims, No Drawings

FAST DECOMPOSING PELLETS

The invention concerns pharmaceutical forms of administration that are in the form of pellets which contain at least one rounding agent required to produce extrusion pellets which acts as a retardant or disintegration-retarding agent which is suitable for delaying the release time of active substances, wherein the release of the active substance from the pellet (pellet A) is not less than that of a corresponding reference core pellet (pellet B) which does not contain this rounding agent as a pharmaceutical auxiliary substance. The release rate of these rapidly disintegrating pellets is at least about 90% within a time period of 30 minutes. In addition the present invention also concerns processes for the production these pellets.

Pellets are usually used for modified release drug forms. They have considerable advantages compared to conventional pharmaceuticals with a modified release of the active substance such as e.g. the avoidance of dose-dumping and local intolerances, minimized intra- and interindividual variations, independent of stomach emptying times, mixing of various retarded pellets, mixing of pellets with different (optionally incompatible) active substances and improvement of bioavailability.

The following principles are often used to produce pellets with a modified release of the active substance: a) modification of the active substance release with the aid of coatings or b) matrix systems.

Coatings that are resistant to gastric juice are stable in the acidic environment of the stomach and slowly dissolve by salt formation in a weakly acidic or basic range. Since, however, pellets are substantially independent of the stomach emptying rhythms, gastric juice-resistant coatings only lead to a short-term delay of the release of active substance.

Coatings are also used which are insoluble in the gastrointestinal tract and release the dissolved active substance by means of diffusion through the coat. In this case the release rate can for example be set by means of the diffusion coefficients, the film thickness, the concentration gradient, the osmotic pressure and the use of pore formers. However, in the case of poorly soluble active substances the amount of liquid diffusing through the coat into the core is not sufficient to dissolve the active substance so that only a part of the total dose is released.

In order to circumvent these disadvantages time-controlled systems have been developed in recent years in which the envelope bursts after a certain delay time. The release profile can be adjusted by mixing pellet collectives with various coatings. These systems are distinguished by being independent of intraindividual and interindividual variations, they release the complete dose of active substance and are suitable for readily soluble as well as for poorly soluble pharmaceutical substances.

Milosovich (U.S. Pat. No. 3,247,066) developed a drug form with controlled release of the active substance based on small pellets which contain a colloid that swells in water and are coated with an indigestible envelope. Digestive fluid passes into the core containing disintegrant by means of diffusion which then swells and bursts the core.

A further variant of this multilayered so-called time controlled explosion system (abbreviated: TCES) (cf. EP 0 210 540 B1) in which a layer directly under the envelope which contains disintegrant causes the coating to burst.

Bayer AG (patent DD 297 767) developed a pellet formulation with a time controlled release that was produced by rotor granulation. With the aid of a release-controlling double layer composed of an external indigestible lacquer layer and an inner coat which controls the migration of the water towards the core, moisture reaches the core containing disintegrant which then bursts the envelope.

However, the formulations produced in U.S. Pat. No. 3,247,066, in EP 0 210 540 B1 and DD 297 767 were not produced by means of extrusion and rounding so that it was not possible to obtain pellets with a narrow particle-size distribution.

Double-coated granulates are known from EP 0 421 921 B1 which are obtained by extrusion of the wet granulate mass and which are moulded into spherical pellets with a diameter of 0.3 to 1.5 mm. However, these are pellets which achieve a time controlled release by a gastric juice-resistant but intestinal juice-soluble film and not by a burst mechanism.

Although an advantage of extrusion processes over rotor granulation is that a narrow distribution of particle sizes can be achieved, a fundamental disadvantage of extrusion pellets is that it is not possible to dispense with certain pharmaceutical additives such as microcrystalline cellulose for their production since they give the extrudate the required plastic-rigid properties required for rounding. In this case such additives in most cases also act as retarding agents i.e. they lead to a delayed (retarded) release of the active substance. This retardation which is often an inevitable consequence is not desirable in all cases. Retarding agents (in particular microcrystalline cellulose), can form a matrix system which prevents the disintegration of the pellets so that overall pellets with retarding properties with regard to the release of the active substance are obtained. Furthermore the additives used as rounding agents also acts as disintegration retarding agents i.e. they prevent the rapid decay of the pellets into smaller particles. Especially in the case of poorly soluble medicinal substances these effects cause a considerable delay in the release of the active substance and a retardation of the drug release. Hence active substances that have a strongly pH-dependent solubility profile and which are poorly soluble especially in the basic intestinal juice are characterized by the formation of a dense matrix system with microcrystalline cellulose. In such cases the release profile cannot be varied as desired by means of the composition and the thickness of the coating since the leaching of the drug from the matrix and the rate of disintegration of the pellets play an important role in the release properties.

Therefore the object of the invention was to provide such pellets that rapidly disintegrate and release the active substance in as short a time as possible from the core pellets although the pellets contain rounding aids which among others act as retarding agents and/or as disintegrating retarding agent.

It was surprisingly found that pellet cores which contain a) a rounding agent acting as a retarding agent or as a disintegration-retarding agent b) a tablet disintegrant (also referred to as intensive disintegrant in the following) and c) at least one auxiliary substance selected from the group comprising surfactants and binding agents and d) optionally fillers or combinations of these auxiliary substances, disintegrate well. Furthermore the corresponding active substances are rapidly released from the core pellets and essentially without delay compared to a pellet which does not have this rounding agent or retarding agent. This applies particularly to poorly soluble active substances. In particular the core pellets contain an intensive disintegrant, a surfactant and a binding agent in addition to the rounding agent. It is also possible to use a binding agent e.g. polyvinylpyrrolidone (PVP) instead of the surfactant. In a preferred variant a PVP is additionally added to the pellet core in addition to the surfactant.

A further advantage of the pellets according to the invention is that they have a narrow particle size distribution: At least 90% of the particles have a diameter of about 0.6–1.2 mm. Moreover the pellets also disintegrate relatively rapidly when they contain active substances which have a strong pH-dependent solubility profile. The pellets usually have a diameter between 0.5–2 mm, depending on the perforated disk used for the extrusion.

The rapidly disintegrating pellets according to the invention (also referred to as core pellet A in the following) have a release rate of the active substance which is not delayed despite the presence of the rounding agent that acts as a retarding agent or disintegration-retarding agent. The release of the active substance is essentially not retarded. The release is relatively rapid and, in particular, it is comparable with the pellet which can be produced by an alternative process to the extrusion process and which does not contain this retarding agent or disintegration-retarding agent (also referred to as core pellet B in the following or reference pellet). The core pellets according to the invention do not have a delayed release of the active substance. The release rate of such core pellets is preferably at least 90% after 30 minutes.

The pellets according to the invention (core pellets A) contain the common pharmaceutical disintegrants preferably in an amount of 5–50% and surfactants in an amount of 0.1–20%. Binding agents can be advantageously added in an amount of 1–10%. Microcrystalline cellulose (e.g. Avicel®) as a rounding aid is in particular present in an amount of 5–70%. The percentages refer to the weight percentages of the pellet cores if not stated otherwise.

Rounding agents that are suitable for the production of extrusion pellets are all common auxiliary substances known in the literature which enable a rounding of the pharmaceutical mass obtained by extrusion primarily in a rod shape. Microcrystalline cellulose and derivatives thereof such as e.g. Avicel®, Avicel® PH 101, Avicel® PH 105 or Avicel® PH 200 are for example suitable. Provided these rounding aids delay the release of the active substance compared to other pellets which do not contain this auxiliary substance or provided these rounding aids delay the disintegration of the pellets into smaller particles (disintegration-retarding agents), they are suitable within the sense of the present invention as so-called retarding agents for the production of the core pellets according to the invention.

All common pharmaceutical binding agents come into consideration as binding agents e.g. gelatin, microcrystalline cellulose, L-HPC, starch, standard hydroxypropylmethyl cellulose derivatives and polyvinylpyrrolidone (PVP) derivatives. However, polyvinylpyrrolidone (PVP) derivatives are particularly preferred as binding agents since these do not impair but rather favour the disintegration of the pellets despite having excellent binding properties so that according to the invention it is even possible to omit the surfactant if PVP is used in combination with an intensive disintegrant.

All standard pharmaceutical auxiliary substances can be used as tablet disintegrants (disintegration aids) or intensive disintegrants for pharmaceutical purposes which have strong swelling properties in aqueous media and which are distinguished by volume enlargement through the uptake of water. The term tablet disintegrant relates to those pharmaceutical auxiliary substances which enable rapid disintegration of tablets in water or in gastric juice and that enable the release of drugs in absorbable form. Depending on the mechanism of action these are substances that increase the porosity of solid forms of administration and have a large absorption ability for water (starch, cellulose derivatives, alginates, dextrans, cross-linked polyvinylpyrrolidone and others), as well as wetting agents that allow wetting of the solid forms of administration (such as e.g. polyethylene glycol sorbitan fatty acid ester). Sodium carboxymethyl cellulose, modified corn starch (e.g. Starch®1500) and sodium carboxymethyl starch (Explotab® or Primojel®) are preferably used. Primojel® is particularly preferred.

Standard pharmaceutical surface active substances are used as surfactants such as ionic and non-ionic surfactants, such as benzalkonium chloride, polyoxyethylene-polyoxypropylene copolymers (e.g. Pluronic® F68), polyethylene glycol glycerol ester, alkyl sulfates, preferably sodium dodecylsulfate (Texapon®) and stearic acid or alkali or alkaline earth salts thereof (Mg or Na salts) or stearates such as e.g. PEG-400-stearate (Mirj®).

Optionally one or several standard pharmaceutical fillers are also added. The amount of filler can be up to 80%. Fillers that are used according to the invention are carbohydrates such as sugars preferably glucose, lactose and sucrose, sugar alcohols such as mannitol and sorbitol, starch, starch derivatives and dibasic calcium phosphate. However, all known fillers are in principle suitable.

Particularly preferred formulations according to the invention comprise 15–25% microcrystalline cellulose, 15–25% disintegrant, 2–10% surfactant and/or 3–7% polyvinylpyrrolidone (all data in % by weight) as well as optionally further binders or fillers.

Active substances within the sense of the invention are basically all drugs that come into consideration for the therapeutic treatment of humans. Those active substances are preferred that are poorly soluble. Poorly soluble active substances within the sense of the present invention are those that are referred to in general pharmacopeias (e.g. USP XXII) as not easily soluble active substances. Such active substances have for example a solubility of less than 0.1 mg/ml, in particular of less than 0.05 mg/ml or less than 0.01 mg/ml in an aqueous medium or whose solubility properties are strongly pH dependent. Active substances are for example (±)-1-(9H-carbazol-4-yloxy)-3-[(2-(2-methoxyphenoxy)-ethyl)-amino]-2-propanol (INN: Carvedilol), 2-{4-[2-[(4-chloro-benzoyl)-amino]ethyl]phenoxy}-2-methylpropionic acid (INN: Bezafibrat), INN: Glibenclamid or 1-isopropyl-3-[(4-m-toluidino-3-pyridyl)sulfonyl]-urea (INN: Torasemid). These active substances are poorly soluble. In particular Carvedilol has a strongly pH-dependent solubility profile and is particularly poorly soluble in the intestinal juice. However, these substances and in particular Carvedilol are released very well from the pellets according to the invention.

In order to check the disintegration of pellets it is possible to use generally known methods and instruments that are described in standardized form in pharmacopeias. A standardized paddle apparatus (37° C., 90 rpm) can therefore be used to measure the disintegration time. The disintegration time is stopped as soon as 90% of the pellets have disintegrated into smaller agglomerates. The release rate of the active substance (data in % in relation to a certain unit of time) is also determined according to generally standardized methods (cf. European pharmacopoiea or US Pharmacopoiea).

Surprisingly the pellets according to the invention have a disintegration rate of at least 90% after 30 minutes and already after 20, 10 or 5 or 2 minutes in the case of particularly preferred embodiments. At least 90% of the active substance has been released after 30 minutes. After 10 minutes the active substance has been released from the core pellets by at least 50%, preferably at least 70% and especially by at least 90%. Surprisingly it was also possible to achieve these release rates with poorly soluble active substances. The release is determined in an aqueous medium, the pH of the solution being adjusted to a value at which the active substance has an optimal solubility.

Thus Texapon® and Carvedilol pellets containing disintegrant have already disintegrated even after 2 minutes and already exhibit ca. 70% release of active substance after 5 minutes. The disintegration is advantageously further accelerated by the use of Pluronic® F 68 so that already after 5 minutes more than 90% of the Carvedilol has been released. These pellet cores according to the invention which have not been coated are thus suitable as alternatives to a non-retarded monolithic pharmaceutical form.

Pellets according to the invention particularly advantageously contain a combination of a tablet disintegrant together with either a surfactant and/or a binding agent. It is particularly preferred to combine a disintegrant with a surfactant or to combine a disintegrant with a binding agent. The addition of a combination of a disintegrant with one of the auxiliary substances mentioned (surfactant and/or binding agent) leads to a better release rate than the addition of disintegrant alone (cf. Tables 1 and 2).

The pellets according to the invention are produced by mixing the active substances with the pharmaceutical auxiliary substances 1, and subsequently granulating, extruding and rounding. The extrusion/rounding process according to the invention enables in contrast to rotor granulation the pellets to be produced with a very narrow particle size distribution. If a perforated disk is used with a hole diameter of 1 mm, about 90% of the pellets have a diameter of about 0.6–1.2 mm.

For the production of the pellets according to the invention a neutral starter core is not necessary it is possible to incorporate much larger doses of active substance. According to the invention amounts of active substance of up to at least 80% (% by weight) are feasible. The amount of active substance is preferably for example at least 30%, 50% or 70%. Carvedilol pellets can be produced without any difficulty within the sense of the present invention with a content of active substance of 70% and these decay in less than 10 minutes, in particular less than 5 minutes or less than 2 minutes.

In a special embodiment the core pellets according to the invention can also be coated with coatings e.g. to modify the release of active substance or to cover an unpleasant taste. In the sense of the present invention the rapidly disintegrating core pellets can also be provided with a coating in order to develop time-controlled systems by coating the rapidly disintegrating swelling pellets according to the invention in which the coating bursts after a certain delay time. The core formulations according to the invention are particularly well suited as a base for the development of a drug form with a modified release of active substance in which a time-controlled release of the active substance is achieved by the bursting of a film since the swelling pressure that develops in the pellet core after uptake of moisture is sufficient to tear open an indigestible coating. Especially in the case of poorly water-soluble pharmaceutical substances such burst systems offer the advantage over diffusion pellets that the dose of active substance is released relatively rapidly and completely from the drug form. The delay time can be varied between 10 minutes and 5 hours by the composition and the film coating thickness of the film as well as by the formulation of the rapidly disintegrating core.

It is known that a thick film layer alone can delay the start of release for a long time, this however, results in a slower release of active substance after the coating bursts. Larger amounts of coating additionally require more time to apply the coating which is uneconomical. Surprisingly the film coating thickness of the pellets according to the invention can be kept relatively low by selection of suitable film additives.

The rapidly disintegrating pellets can additionally be coated with readily soluble films (e.g. hydroxypropyl methylcellulose) or with films which dissolve pH-dependently in the gastrointestinal tract (gastric juice-resistant coatings). The pellets can also be coated with layers of various film formers or various formulations of the same film former. Coated pellets which release the active substance after various delay times as well as rapidly disintegrating non-coated pellets can be mixed in order to achieve diverse release profiles (e.g. pulsed release, release according to a 0 order kinetics or nth order kinetics, sigmoidal release). The rapidly disintegrating pellets can be coated by common pharmaceutical methods e.g. in a fluidized bed or coating pan.

Calculated from the time that the release begins, the coated rapidly disintegrating pellets according to the invention have a release of at least 50% after 180 minutes. The amount of coating applied can be varied such that the proportion by weight of the film former is between 1 and 70% relative to the pellet core weight.

Preferred coating materials for the production of coated pellets whose film is burst by the swelling of the pellet core are preferably ethyl cellulose e.g. Aquacoat® and methacrylic ester copolymers e.g. Eudragit® RL/ RS. Materials that can be used for readily soluble films are e.g. cellulose derivatives (such as e.g. hydroxypropylmethyl cellulose) or amino-alkylmethacrylate copolymers (e.g. Eudragit® E). Dicarboxylic acid derivatives of cellulose compounds (e.g. hydroxypropylmethyl cellulose phthalate, hydroxypropylmethyl cellulose succinate) as well as methacrylic acid copolymers (e.g. Eudragit® L, Eudragit® S) are suitable as film formers for pH-dependent soluble coatings.

The following film additives can be used: Softening agents in an amount of 0.1–50%, detackifiers (0.1–70%) as well as, especially in the case of films that are burst by the swelling of the pellet core, substances which can accelerate or delay the diffusion of the release liquid into the core and can consequently modify the delay time until the release of active substance starts (0.1–50%). Furthermore it is possible to add pore formers, aroma substances, dyes, pigments as well as fillers.

All common pharmaceutical softening agents can be used as softening agents. Acetylated fatty acid glycerides, acetyl-triethyl citrate, acetyl-tributyl citrate, dibutyl phthalate, diethyl phthalate, dimethyl phthalate, glycerol triacetate, propylene glycol, polyethylene glycol, polyoxyethylene-polyoxypropylene copolymers, castor oil and tributyl citrate are preferred. Triethyl citrate is particularly preferred.

All common pharmaceutical detackifiers can be used as detackifiers. Talcum, Aerosil®, kaolin and micronized silicic acid are preferred. Glycerol esters and ethers of higher fatty acids e.g. glycerol monostearate, polyethylene glycol-32-glyceryl laurate are particularly preferred.

Additives that come into consideration that can control the diffusion of water into the pellet core are hydrophobizing additives (e.g. waxes, talcum, fatty acids and fatty acid esters) as well as substances that accelerate diffusion (e.g. surfactants, fatty acid esters and fatty acid ethers). Montan-glycol wax, glycerol monostearate, stearic acid and stearic acid derivatives and polyethylene glycol-glyceryl esters, glycerylbehenate, glycerylpalmito-stearate, cetyl palmitate are particularly preferred.

The coated and/or non-coated pellets according to the invention can be pressed according to known processes into tablets also together with standard pharmaceutical auxiliary substances or be filled into capsules or sachets or embedded in matrices. The formulations are equally suitable for readily and poorly water-soluble active substances. The capsules contain the active substance in an amount of up to 350 mg, in particular 1–200 mg, preferably 10–100 mg. Pellet tablets can contain the active substance in an amount of up to 1000 mg, preferably 1–500 mg and in particular 10–250 mg.

Finally it is intended to elucidate the invention in more detail by the application examples.

APPLICATION EXAMPLES

Example 1

1250 g Carvedilol, 1682.5 g lactose, 1150 g microcrystalline cellulose, 172.5 g sodium dodecyl sulfate, 345 g Povidon K 25 and 1150 g Primojel are homogenized in an intensive mixer. The powder mixture is granulated in ca. 3500 ml distilled water. Subsequently the wet mass is extruded in a (twin-screw) extruder at room temperature. The extrudate is then formed into pellets in a rounder. After drying on a fluidized bed, the pellets are screened (mesh size 0.6–1.25 mm).

Example 2

Pellets of the following formulation are produced analogously to example 1:

|  | Parts by weight |
| --- | --- |
| Carvedilol | 21.75 |
| hydroxypropylmethylcellulose 2910 | 3.00 |
| lactose | 29.25 |
| microcrystalline cellulose | 20.00 |
| sodium dodecylsulfate | 3.00 |
| Povidon K 25 | 3.00 |
| Primojel | 20.00 |
| distilled water | 66.70 |

Example 3

Pellets of the following formulation are produced analogously to example 1:

|  | Parts by weight |
| --- | --- |
| Carvedilol | 21.75 |
| hydroxypropylmethylcellulose 2910 | 3.00 |
| lactose | 37.25 |
| microcrystalline cellulose | 20.00 |
| sodium dodecylsulfate | 3.00 |
| Primojel | 15.00 |
| distilled water | 53.85 |

Example 4

Pellets of the following formulation are produced analogously to example 1:

|  | Parts by weight |
| --- | --- |
| Carvedilol | 21.75 |
| lactose | 39.25 |
| microcrystalline cellulose | 10.00 |
| sodium dodecylsulfate | 3.00 |
| Povidon K 25 | 6.00 |
| Primojel | 20.00 |
| distilled water | 45.00 |

Example 5

Pellets of the following formulation are produced analogously to example 1:

|  | Parts by weight |
| --- | --- |
| Carvedilol | 21.75 |
| lactose | 9.25 |
| microcrystalline cellulose | 40.00 |
| sodium dodecylsulfate | 3.00 |
| Povidon K 25 | 6.00 |
| Primojel | 20.00 |
| distilled water | 81.80 |

Example 6

Pellets of the following formulation are produced analogously to example 1:

|  | weight percentage |
| --- | --- |
| Carvedilol | 21.75 |
| lactose | 49.25 |
| microcrystalline cellulose | 10.00 |
| sodium dodecylsulfate | 3.00 |
| Povidon K 25 | 6.00 |
| Primojel | 10.00 |
| distilled water | 43.00 |

Example 7

Pellets of the following formulation are produced analogously to example 1:

|  | weight percentage |
| --- | --- |
| Carvedilol | 21.75 |
| lactose | 19.25 |
| microcrystalline cellulose | 20.00 |
| sodium dodecylsulfate | 3.00 |
| Povidon K 25 | 6.00 |
| Primojel | 30.00 |
| distilled water | 66.70 |

Example 8

Pellets of the following formulation are produced analogously to example 1:

|  | weight percentage |
|---|---|
| Carvedilol | 21.75 |
| lactose | 29.25 |
| microcrystalline cellulose | 20.00 |
| sodium dodecylsulfate | 3.00 |
| Povidon K 25 | 6.00 |
| starch 1500 | 20.00 |
| distilled water | 33.30 |

Example 9

Pellets of the following formulation are produced analogously to example 1:

|  | weight percentage |
|---|---|
| Carvedilol | 43.50 |
| lactose | 7.5 |
| microcrystalline cellulose | 20.00 |
| sodium dodecylsulfate | 3.00 |
| Povidon K 25 | 6.00 |
| Primojel | 20.00 |
| distilled water | 58.70 |

Example 10

Pellets of the following formulation are produced analogously to example 1:

|  | weight percentage |
|---|---|
| Carvedilol | 21.75 |
| hydroxypropylmethylcellulose 2910 | 3.00 |
| lactose | 22.25 |
| microcrystalline cellulose | 20.00 |
| sodium dodecylsulfate | 5.00 |
| Primojel | 20.00 |
| distilled water | 69.50 |

Example 11

|  | weight percentage |
|---|---|
| Carvedilol | 21.75 |
| lactose | 31.75 |
| microcrystalline cellulose | 20.00 |
| Pluronic F 68 | 0.50 |
| Povidon K 25 | 6.00 |
| Primojel | 20.00 |
| distilled water | 43.00 |

Carvedilol, lactose, microcrystalline cellulose, Primojel and Povidon K 25 are mixed. Pluronic F 68 is dissolved in distilled water. The powder mixture is granulated with this solution. Subsequently it is extruded, rounded, dried and screened analogously to example 1.

Example 12

|  | weight percentage |
|---|---|
| Carvedilol | 21.75 |
| lactose | 31.25 |
| microcrystalline cellulose | 20.00 |
| Pluronic F 68 | 1.00 |
| Povidon K 25 | 6.00 |
| Primojel | 20.00 |
| distilled water | 43.00 |

Carvedilol, lactose, microcrystalline cellulose, Primojel and Povidon K 25 are mixed. Pluronic F 68 is dissolved in distilled water. The powder mixture is granulated with this solution. Subsequently it is extruded, rounded, dried and screened analogously to example 1.

Example 13

|  | weight percentage |
|---|---|
| Carvedilol | 21.75 |
| lactose | 30.25 |
| microcrystalline cellulose | 20.00 |
| Pluronic F 68 | 2.00 |
| Povidon K 25 | 6.00 |
| Primojel | 20.00 |
| distilled water | 43.00 |

Carvedilol, lactose, microcrystalline cellulose, Primojel and Povidon K 25 are mixed. Pluronic F 68 is dissolved in distilled water. The powder mixture is granulated with this solution. Subsequently it is extruded, rounded, dried and screened analogously to example 1.

Example 14

|  | weight percentage |
|---|---|
| Carvedilol | 21.75 |
| lactose | 29.25 |
| microcrystalline cellulose | 20.00 |
| Pluronic F 68 | 3.00 |
| Povidon K 25 | 6.00 |
| Primojel | 20.00 |
| distilled water | 64.00 |

Carvedilol, lactose, microcrystalline cellulose, Primojel and Povidon K 25 are mixed. Pluronic F 68 is dissolved in distilled water. The powder mixture is granulated with this solution. Subsequently it is extruded, rounded, dried and screened analogously to example 1.

Example 15

|  | weight percentage |
|---|---|
| Carvedilol | 21.75 |
| lactose | 27.25 |
| microcrystalline cellulose | 20.00 |
| Pluronic F 68 | 5.00 |

-continued

|  | weight percentage |
|---|---|
| Povidon K 25 | 6.00 |
| Primojel | 20.00 |
| distilled water | 33.00 |

Carvedilol, lactose, microcrystalline cellulose, Primojel and Povidon 25 are mixed. Pluronic® F 68 is dissolved in distilled water. The powder mixture is granulated with this solution. Subsequently it is extruded, rounded, dried and screened analogously to example 1.

Example 16

|  | weight percentage |
|---|---|
| Carvedilol | 21.75 |
| lactose | 29.25 |
| microcrystalline cellulose | 20.00 |
| Mirj | 3.00 |
| Povidon K 25 | 6.00 |
| Primojel | 20.00 |
| distilled water | 61.00 |

Carvedilol, lactose, microcrystalline cellulose, Primojel and Povidon K 25 are mixed. Mirj is dissolved in distilled water. The powder mixture is granulated with this mixture. Subsequently it is extruded, rounded, dried and screened analogously to example 1.

Example 17

Pellets of the following formulation are produced analogously to example 1:

|  | weight percentage |
|---|---|
| Carvedilol | 21.75 |
| lactose | 24.25 |
| microcrystalline cellulose | 20.00 |
| sodium dodecylsulfate | 3.00 |
| polyethylene glycol-32-glyceryl laurate | 3.00 |
| Povidon K 25 | 6.00 |
| Primojel | 20.00 |
| distilled water | 43.00 |

Carvedilol, lactose, microcrystalline cellulose, sodium dodecylsulfate, Povidon K 25 and Primojel are mixed. Polyethylene glycol-32-glyceryl laurate is dissolved in distilled water. The powder mixture is granulated with this mixture. Subsequently it is extruded, rounded, dried and screened analogously to example 1.

Example 18

Pellets of the following formulation are produced analogously to example 1:

|  | weight percentage |
|---|---|
| Carvedilol | 21.75 |
| glucose | 29.25 |
| microcrystalline cellulose | 20.00 |
| sodium dodecylsulfate | 3.00 |
| Povidon K 25 | 6.00 |
| Primojel | 20.00 |
| distilled water | 42.85 |

Example 19

Pellets of the following formulation are produced analogously to example 1:

|  | weight percentage |
|---|---|
| Carvedilol | 21.75 |
| hydroxypropylmethylcellulose 2910 | 3.00 |
| microcrystalline cellulose | 20.00 |
| sodium dodecylsulfate | 3.00 |
| Primojel | 15.00 |
| sucrose | 37.25 |
| distilled water | 42.85 |

Example 20

Pellets of the following formulation are produced analogously to example 1:

|  | weight percentage |
|---|---|
| lactose | 71.00 |
| microcrystalline cellulose | 10.00 |
| sodium dodecylsulfate | 3.00 |
| Povidon K 25 | 6.00 |
| Primojel | 10.00 |
| distilled water | 20.50 |

Example 21

Pellets of the following formulation are produced analogously to example 1:

|  | weight percentage |
|---|---|
| Glibenclamid | 21.75 |
| lactose | 29.25 |
| microcrystalline cellulose | 20.00 |
| sodium dodecylsulfate | 3.00 |
| Povidon K 25 | 6.00 |
| Primojel | 20.00 |
| distilled water | 25.00 |

Example 22

Pellets of the following formulation are produced analogously to example 1:

|  | weight percentage |
|---|---|
| Carvedilol | 21.75 |
| lactose | 32.25 |
| microcrystalline cellulose | 20.00 |
| Povidon K 25 | 6.00 |
| Primojel | 20.00 |
| distilled water | 72.40 |

Example 23

Only one disintegrant (no surfactant) was used as a reference but which alone did not enable the pellets to disintegrate. Pellets of the following formulation are produced analogously to example 1:

|  | weight percentage |
|---|---|
| Carvedilol | 21.75 |
| hydroxypropylmethylcellulose 2910 | 3.00 |
| lactose | 40.25 |
| microcrystalline cellulose | 20.00 |
| Primojel | 15.00 |
| distilled water | 53.85 |

TABLE 1

| Example | Appearance | Disintegration [min] | Release >90% [min] |
|---|---|---|---|
| 1 | ++ | <5 | 10–15 |
| 2 | ++ | <5 | 15–20 |
| 3 | ++ | <5 | 20 |
| 4 | ++ | <5 | 12 |
| 5 | ++ | <5 | 20 |
| 6 | + | <3 | n.d. |
| 7 | – | 10 | 30–40 |
| 8 | ++ | <5 | n.d. |
| 9 | ++ | <3 | 25 |
| 10 | ++ | 3 | 25 |
| 11 | ++ | 2 | n.d. |
| 12 | ++ | <2 | n.d. |
| 13 | ++ | <2 | n.d. |
| 14 | ++ | <2 | 5 |
| 15 | ++ | <2 | n.d. |
| 16 | ++ | <3 | 10 |
| 17 | ++ | <3 | 5–10 |
| 18 | 0 | <5 | n.d. |
| 19 | ++ | <10 | 30 |
| 20 | + | <5 | n.d. |
| 21 | + | <5 | n.d. |
| 22 | ++ | 4 | 20 |
| 23 | ++ | no disintegration | 120 |

Legend for table 1: ++ round
+ round oval
0 oval - oval-rod-like
− rods
n.d. not determined

Example 24

With the following composition of the formulation the pellets disintegrated within less than 3 minutes:

| Components of the formulation | weight percentage | disintegration |
|---|---|---|
| Carvedilol | 70% | <3 minutes |
| lactose D200 | 1% | |
| microcrystalline cellulose | 10% | |
| PVP K 25 | 6% | |
| sodium carboxymethyl starch | 10% | |
| sodium dodecylsulfate | 3% | |
| water | 39% | |

Example 25

With the following composition of the formulation in which the content of Carvedilol is below 25% no disintegration of the pellets is observed.

| | | |
|---|---|---|
| Carvedilol | 21.75% | no disintegration |
| lactose D200 | 49.25% | |
| microcrystalline cellulose | 20% | |
| PVP K 25 | 6% | |
| sodium dodecylsulfate | 3% | |
| water | 22% | |

Example 26

The following formulation is prepared analogously to example 24 in which the amount of sodium dodecylsulfate is omitted and the amount of lactose is increased accordingly. No disintegration of the pellets is observed.

| | | |
|---|---|---|
| Carvedilol | 21.75% | no disintegration |
| lactose | 52.25% | |
| microcrystalline cellulose | 20% | |
| PVP K 25 | 6% | |
| water | 22% | |

Example 27

Rapidly disintegrating pellets according to example 1 are coated in the fluid bed (Hüttlin ball coater) with a film of the following composition:

| Components of the formulation | weight percentage relative to the pellet core weight [%] |
|---|---|
| ethylcellulose (Aquacoat ®) | 15% |
| triethyl citrate | 3% |
| glycerol monostearate | 0.75% |
| distilled water | q.s. |

Example 28

Rapidly disintegrating pellets according to example 1 are coated in the fluid bed (Hüttlin ball coater) with a film of the following composition:

| Components of the formulation | weight percentage relative to the pellet core weight |
|---|---|
| ethylcellulose (Aquacoat ®) | 20% |
| triethyl citrate | 4% |
| glycerol monostearate | 1% |
| distilled water | q.s. |

Example 29

Rapidly disintegrating pellets according to example 1 are coated in the fluid bed (Hüttlin ball coater) with a film of the following composition:

| Components of the formulation | weight percentage relative to the pellet core weight |
|---|---|
| ethylcellulose (Aquacoat ®) | 25% |
| triethyl citrate | 5% |
| glycerol monostearate | 1.25% |
| distilled water | q.s. |

Example 30

Rapidly disintegrating pellets according to example 1 are coated in the fluid bed (Hüttlin ball coater) with a film of the following composition:

| Components of the formulation | weight percentage relative to the pellet core weight |
|---|---|
| ethylcellulose (Aquacoat ®) | 20% |
| triethyl citrate | 4% |
| stearic acid | 2% |
| distilled water | q.s. |

Example 31

Rapidly disintegrating pellets according to example 1 are coated in the fluid bed (Hüttlin ball coater) with a film of the following composition:

| Components of the formulation | weight percentage relative to the pellet core weight |
|---|---|
| ethylcellulose (Aquacoat ®) | 20% |
| triethyl citrate | 4% |
| PEG-32-glyceryl laurate | 2% |
| distilled water | q.s. |

Example 32

Rapidly disintegrating pellets according to example 1 are coated in the fluid bed (Hüttlin ball coater) with a film of the following composition:

| Components of the formulation | weight percentage relative to the pellet core weight |
|---|---|
| ethylcellulose (Aquacoat ®) | 20% |
| triethyl citrate | 4% |
| montanglycol wax | 3% |
| distilled water | q.s. |

Example 33

Rapidly disintegrating pellets according to example 1 are coated in the fluid bed (Hüttlin ball coater) with a film of the following composition:

| Components of the formulation | weight percentage relative to the pellet core weight |
|---|---|
| ethylcellulose (Aquacoat ®) | 20% |
| triethyl citrate | 4% |
| talcum | 10% |
| distilled water | q.s. |

Example 34

Rapidly disintegrating pellets according to example 1 are coated in the fluid bed (Hüttlin ball coater) with a film of the following composition:

| Components of the formulation | weight percentage relative to the pellet core weight |
|---|---|
| ethylcellulose (Aquacoat ®) | 20% |
| triethyl citrate | 4% |
| montanglycol wax | 3% |
| distilled water | q.s. |

Example 35

Rapidly disintegrating pellets according to example 1 are coated in the fluid bed (Hüttlin ball coater) with a film of the following composition:

| Components of the formulation | weight percentage relative to the pellet core weight |
|---|---|
| PEG-32-glyceryl laurate | 2.5% |
| distilled water | q.s. |

Subsequently a film with the following composition is applied:

| Components of the formulation | weight percentage relative to the pellet core weight |
|---|---|
| ethylcellulose (Aquacoat ®) | 20% |
| triethyl citrate | 4% |
| montanglycol wax | 3% |
| distilled water | q.s. |

Example 36

Rapidly disintegrating pellets according to example 1 are coated in the fluid bed (Hüttlin ball coater) with a film of the following composition:

| Components of the formulation | weight percentage relative to the pellet core weight[%] |
|---|---|
| ethylcellulose (Aquacoat ®) | 20% |
| triethyl citrate | 4% |
| montanglycol wax | 3% |
| PEG-32-glyceryl laurate | 2% |
| distilled water | q.s. |

Example 37

Rapidly disintegrating pellets according to example 1 are coated in the fluid bed (Hüttlin ball coater) with a film of the following composition:

| Components of the formulation | weight percentage relative to the pellet core weight |
|---|---|
| Eudragit RS | 20% |
| triethyl citrate | 4 |
| glycerol monostearate | 0.75% |
| distilled water | q.s. |

Example 38

Rapidly disintegrating pellets according to example 1 are coated in the fluid bed (Hüttlin ball coater) with a film of the following composition:

| Components of the formulation | weight percentage relative to the pellet core weight |
|---|---|
| hydroxypropylmethyl cellulose 2910 | 5% |
| glycerol monostearate | 0.5% |
| Macrogol 6000 | 1% |
| distilled water | q.s. |

Example 39

Rapidly disintegrating pellets according to example 1 are coated in the fluid bed (Hüttlin ball coater) with a film of the following composition:

| Components of the formulation | weight percentage relative to the pellet core weight[%] |
|---|---|
| Eudragit L 30 D | 10% |
| triethyl citrate | 0.5% |
| glycerol monostearate | 0.05% |
| Polysorbat 80 | 0.01% |
| distilled water | q.s. |

TABLE 2

| Example | delay time [min] | release >50% [min] (calculated from the time of active substance release) |
|---|---|---|
| 27 | 40 | 50 |
| 28 | 120 | 120 |
| 29 | 180 | 150 |
| 30 | 180 | 120 |
| 31 | 60 | 40 |
| 32 | 180 | 100 |
| 33 | 100 | 80 |
| 34 | 50 | 30 |
| 35 | 15 | 5 |
| 36 | 90 | 45 |
| 37 | 40 | 120 |
| 38 | 5 | 10 |
| 39 | >120 min in artificial gastric juice | 10 min in artificial intestinal juice |

What is claimed is:

1. A pharmaceutical composition consisting essentially of pellets containing (a) an active substance, (b) 5–70% by weight rounding agent which acts as an active-substance-release retardant or a particle-disintegration retardant, (c) 5–50% by weight tablet disintegrant and (d) at least one of (1) 0.1–20% by weight surfactant and (2) 1–10% by weight binding agent, wherein the pellets have a diameter of between 0.5 and 2 mm.

2. The pharmaceutical composition of claim 1, wherein the pellets contain both a surfactant and a binding agent.

3. The pharmaceutical composition of claim 2, wherein the binding agent is a polyvinylpyrrolidone.

4. The pharmaceutical composition of claim 1, wherein the pellets contain only a binding agent as component (d).

5. The pharmaceutical composition of claim 4, wherein the binding agent is a polyvinylpyrrolidone.

6. The pharmaceutical composition of claim 1, wherein the pellets contain only a surfactant as component (d).

7. The pharmaceutical composition of claim 1, wherein at least 90% of the pellets have a diameter of about 0.6 to 1.2 mm.

8. The pharmaceutical composition of claim 1, wherein the release rate of the active substance from the pellets is at least 90% after 30 minutes after administration to a patient.

9. The pharmaceutical composition of claim 1, wherein the pellets contain 15–25% by weight tablet disintegrant.

10. The pharmaceutical composition of claim 1, wherein the pellets contain 2–10% by weight surfactant.

11. The pharmaceutical composition of claim 1, wherein the pellets contain 3–7% by weight binding agent.

12. The pharmaceutical composition of claim 1, wherein the rounding agent is microcrystalline cellulose.

13. The pharmaceutical composition of claim 1, wherein the pellets contain 15–25% by weight microcrystalline cellulose.

14. The pharmaceutical composition of claim 1, wherein the rounding agent is microcrystalline cellulose.

15. The pharmaceutical composition of claim 1, wherein the binding agent is selected from the group consisting of gelatin, microcrystalline cellulose, L-HPC, starch, a hydroxypropylmethyl cellulose and a polyvinylpyrrolidone.

16. The pharmaceutical composition of claim 1, wherein the tablet disintegrant is selected from the group consisting of a starch, a cellulose, an alginate, a dextran, a cross-linked polyvinylpyrrolidone and polyethylene glycol sorbitan fatty acid ester.

17. The pharmaceutical composition of claim 16, wherein the tablet disintegrant is selected from the group consisting of sodium carboxymethyl cellulose, modified corn starch and sodium carboxymethyl starch.

18. The pharmaceutical composition of claim 1, wherein the surfactant is selected from the group consisting of benzalkonium chloride, a polyoxyethylene-polyoxypropylene copolymer, a polyethylene glycol glycerol ester, an alkyl sulfate or an alkali salt thereof, stearic acid or an alkali or alkaline earth salt thereof and a stearate.

19. The pharmaceutical composition of claim 1, wherein the pellets contain (a) an active substance, (b) 15–25% by weight microcrystalline cellulose, (c) 15–25% by weight tablet disintegrant, and (d) 2–10% by weight surfactant and/or 3–7% by weight a polyvinylpyrrolidone.

20. The pharmaceutical composition of claim 1, wherein the active substance is selected from the group consisting of carvedilol, benzafibrat, glibenclamid and torasemid.

21. The pharmaceutical composition of claim 1, wherein the release rate of the pellets is at least 90% after 30 minutes after administration to a patient.

22. The pharmaceutical composition of claim 1, wherein the active substance is present in the pellets in an amount of up to 80% by weight of the pellets.

23. The pharmaceutical composition of claim 1, wherein the binding agent is a polyvinylpyrrolidone.

24. The pharmaceutical composition of claim 1, further comprising a filler selected from the group consisting of a sugar, a sugar alcohol, a starch and dibasic calcium phosphate.

25. The pharmaceutical composition of claim 24, wherein the sugar is selected from the group consisting of glucose, lactose and sucrose.

26. The pharmaceutical composition of claim 24, wherein the sugar alcohol is selected from the group consisting of mannitol and sorbitol.

* * * * *